(12) United States Patent
Ito et al.

(10) Patent No.: US 8,157,777 B2
(45) Date of Patent: Apr. 17, 2012

(54) ABSORBENT PRODUCT FOR PROTECTION OF DISPOSABLE TAPE FROM ULTRAVIOLET RAY

(75) Inventors: Kazuharu Ito, Nishinomiya (JP); Yasuko Shiomichi, Kobe (JP); Dennis San Agustin Casalme, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 300 days.

(21) Appl. No.: 12/211,416

(22) Filed: Sep. 16, 2008

(65) Prior Publication Data

US 2009/0088715 A1   Apr. 2, 2009

Related U.S. Application Data

(60) Provisional application No. 60/995,640, filed on Sep. 27, 2007.

(51) Int. Cl.
*A61F 13/15* (2006.01)
*B65D 73/00* (2006.01)

(52) U.S. Cl. ......... 604/385.02; 604/385.03; 604/385.01; 604/387; 604/389; 604/385.13; 206/494

(58) Field of Classification Search ............. 604/385.01, 604/385.02, 385.03, 387, 389, 385.13; 206/494
See application file for complete search history.

(56) References Cited

U.S. PATENT DOCUMENTS 5,967,665 A   10/1999   MacDonald et al.
6,146,367 A   11/2000   Otsubo et al.
6,352,528 B1   3/2002   Weber et al.
6,610,039 B1   8/2003   Wilhelm et al.
(Continued)

FOREIGN PATENT DOCUMENTS

EP   0 648 483 A1   4/1995
WO   WO 02/096331 A2   12/2002

OTHER PUBLICATIONS

International Search Report, dated Feb. 19, 2009, PCT/IB2008/053920.

(Continued)

*Primary Examiner* — Jacqueline F. Stephens
(74) *Attorney, Agent, or Firm* — Amy M. Foust; Abbey A. Lopez (57) ABSTRACT

An absorbent product comprises (i) a package and (ii) a plurality of absorbent articles contained in the package. The package comprises a first panel and a second panel opposed to the first panel. The package comprises a first window area in the first panel. Each of the absorbent articles has a body facing surface and an external surface opposed to the body facing surface. Each of the absorbent articles has a front region and a rear region opposed to the front region. Each of the absorbent articles comprises a topsheet, a backsheet, an absorbent core disposed between the topsheet and the backsheet, and a disposable tape secured to the external surface of the rear region. Each of the absorbent articles comprises a graphic in the front region and in the rear region. The front region faces the first panel and the rear region faces the second panel. The graphic of the front region is visible through the first window area. As the disposable tape is located in the rear region, the disposable tape faces the second panel. The disposable tape faces away from the first panel, and may be protected from the ultraviolet ray.

5 Claims, 11 Drawing Sheets

U.S. PATENT DOCUMENTS

| | | |
|---|---|---|
| 6,880,313 B1 | 4/2005 | Gessford et al. |
| 6,926,704 B2 | 8/2005 | Andersson et al. |
| 7,021,466 B2 | 4/2006 | Kuske et al. |
| 2003/0106825 A1 | 6/2003 | Molina et al. |
| 2004/0143231 A1 | 7/2004 | Nair et al. |
| 2004/0238393 A1* | 12/2004 | Ohi et al. .................. 206/438 |
| 2005/0090788 A1 | 4/2005 | Shimada et al. |
| 2009/0084698 A1 | 4/2009 | Ito et al. |

OTHER PUBLICATIONS

AA743 International Search Report & Written Opinion, PCT/IB2008/053919, mailed Mar. 27, 2009, 14 pgs.

U.S. Appl. No. 12/211,403, filed on Sep. 16, 2008, Office Action dated Apr. 29, 2009, 12 pgs.

U.S. Appl. No. 12/211,403, filed on Sep. 16, 2008, Office Action dated Nov. 10, 2009, 12 pgs.

U.S. Appl. No. 12/211,403, filed on Sep. 16, 2008, Office Action dated May 26, 2010, 15 pgs.

U.S. Appl. No. 12/211,403, filed on Sep. 16, 2008, Office Action dated May 25, 2011, 8 pgs.

U.S. Appl. No. 12/211,403, filed on Sep. 16, 2008, Office Action dated Sep. 28, 2011, 8 pgs.

* cited by examiner

ABSORBENT PRODUCT FOR PROTECTION OF DISPOSABLE TAPE FROM ULTRAVIOLET RAY

CROSS REFERENCE TO RELATED APPLICATION

This application claims the benefit of U.S. Provisional Application No. 60/995,640, filed Sep. 27, 2007.

FIELD OF THE INVENTION

The present invention relates to an absorbent product comprising a package and a plurality of absorbent articles contained in the package.

BACKGROUND OF THE INVENTION

Disposable absorbent articles are devices which are typically worn in the crotch region of a wearer. The absorbent articles include diapers, training pants, sanitary napkins, pantiliners, incontinent pads, sweat-absorbent underarm pads, nursing pads, human waste management devices and the like. Among them, diapers and training pants, for example, are worn to contain discharged materials such as urines and feces and to isolate these materials from the body of the wearer and from the wearer's surroundings. A wide variety of disposable absorbent articles are currently used for the collection of discharged materials.

Recently, it has been recognized that an absorbent product comprising a package having a transparent or a translucent window is preferred by consumers since such a window can actually show the absorbent articles contained in the package and thus consumers can directly get the information about the absorbent articles through the window. This may be important for recent disposable absorbent articles which have aesthetic features (e.g., a printed graphic thereon) to draw consumers' attention.

It is known in the art that diapers are often provided with a graphic on the backsheet wherein the graphic is visible through a window of a package. Such a package bag is convenient to attract the consumers not only at the markets but also at home.

It has been found that providing a transparent or a translucent window in a package may cause serious problems to the absorbent articles contained therein. For example, diapers in a package which has a transparent or a translucent window may be affected by the ultraviolet ray which comes through the window.

Some diapers are provided with a disposable tape on the external surface. After use, a diaper may contain discharged materials inside. When the user disposes a soiled diaper, the user may roll up the diaper and fix the conformation of the rolled diaper with the disposable tape. However, the disposable tape adhesive used for the disposable tape tends to be vulnerable to the ultraviolet ray. For example, the disposable tape adhesive may be discolored or stiffened when it receives the ultraviolet ray. Discoloration (or yellowing) is perceivable when the diaper is visible through the window of the package. Discoloration is also perceivable after the diaper is taken out of the package. Stiffening is perceivable when the user actually treats the diaper, and stiffening may cause the disposable tape to lose its adhesibility. Furthermore, some retailers build merchandising shelves outside the stores where a sun-shade is not available. When the package having a window is exposed to sunlight, the disposable tape adhesive may be deteriorated if the disposable tape faces the window which allows the transmittance of the ultraviolet ray. Consequently, the appearance and the quality of the diaper may be damaged.

Thus, there is a need for a package which shows a graphic on the diaper in order to appeal to the consumers, and at the same time prevents deterioration of the disposable tape attached to the diaper.

SUMMARY OF THE INVENTION

The present invention relates to an absorbent product comprising (i) a package and (ii) a plurality of absorbent articles contained in the package. The package comprises a first panel and a second panel opposed to the first panel. The package comprises a first window area in the first panel. Each of the absorbent articles has a body facing surface and an external surface opposed to the body facing surface. Each of the absorbent articles has a front region and a rear region opposed to the front region. Each of the absorbent articles comprises a topsheet, a backsheet, an absorbent core disposed between the topsheet and the backsheet, and a disposable tape secured to the external surface of the rear region. Each of the absorbent articles comprises a graphic in the front region and in the rear region. The front region faces the first panel and the rear region faces the second panel. The graphic of the front region is visible through the first window area. The disposable tape is located in the rear region, and it faces the second panel. The disposable tape faces away from the first panel, and it may be protected from the ultraviolet ray if the package is put so that the first panel faces the consumers.

DETAILED DESCRIPTION OF THE INVENTION

Herein, "comprise" and "include" mean that other elements and/or other steps which do not affect the end result can be added. Each of these terms encompasses the terms "consisting of" and "consisting essentially of".

"Absorbent article" refers to articles which absorb and contain discharged materials, and is intended to include diapers, training pants, sanitary napkins, pantiliners, incontinence pads, sweat-absorbent underarm pads, nursing pads, adult incontinence diapers, human waste management devices and the like.

"Disposable" refers to articles which are intended to be discarded after a single use, composted, or otherwise disposed of in an environmentally compatible manner.

"Diaper" refers to a garment generally worn by toddlers and incontinent persons that is worn about the lower torso of the wearer which are intended to absorb and contain the discharged materials from the body (e.g., urine, feces). Diapers include, for example, pull-on diapers and taped diapers. Pull-on diapers refer to diapers which have a defined waist opening and a pair of leg openings and which are pulled onto the body of the wearer by inserting the legs into the leg openings and pulling the article up over the waist. Taped diapers refer to diapers generally include a front and a rear waist section releasably and/or refastenably connected by a fastening system.

"Joined" encompasses configurations in which an element is directly secured to another element by affixing the element directly to the other element; configurations in which the element is indirectly secured to another element by affixing the element to intermediate member(s) which in turn are affixed to the other element; and configurations in which one element is integral with another element, i.e., one element is essentially part of the other element.

"Body facing surface" refers to surfaces of absorbent articles and/or their component members which face the body of the wearer. "External surface" refers to the opposite surfaces of the absorbent articles and/or their component members that face away from the wearer when the absorbent articles are worn.

Absorbent articles and components thereof, including a liquid permeable topsheet, a liquid impermeable backsheet and an absorbent core disposed between the topsheet and the backsheet, and any individual layers of their components, have a body facing surface and an external surface.

In the present invention, "absorbent product" comprises a package and a plurality of disposable absorbent articles contained in the package.

Figure 1:
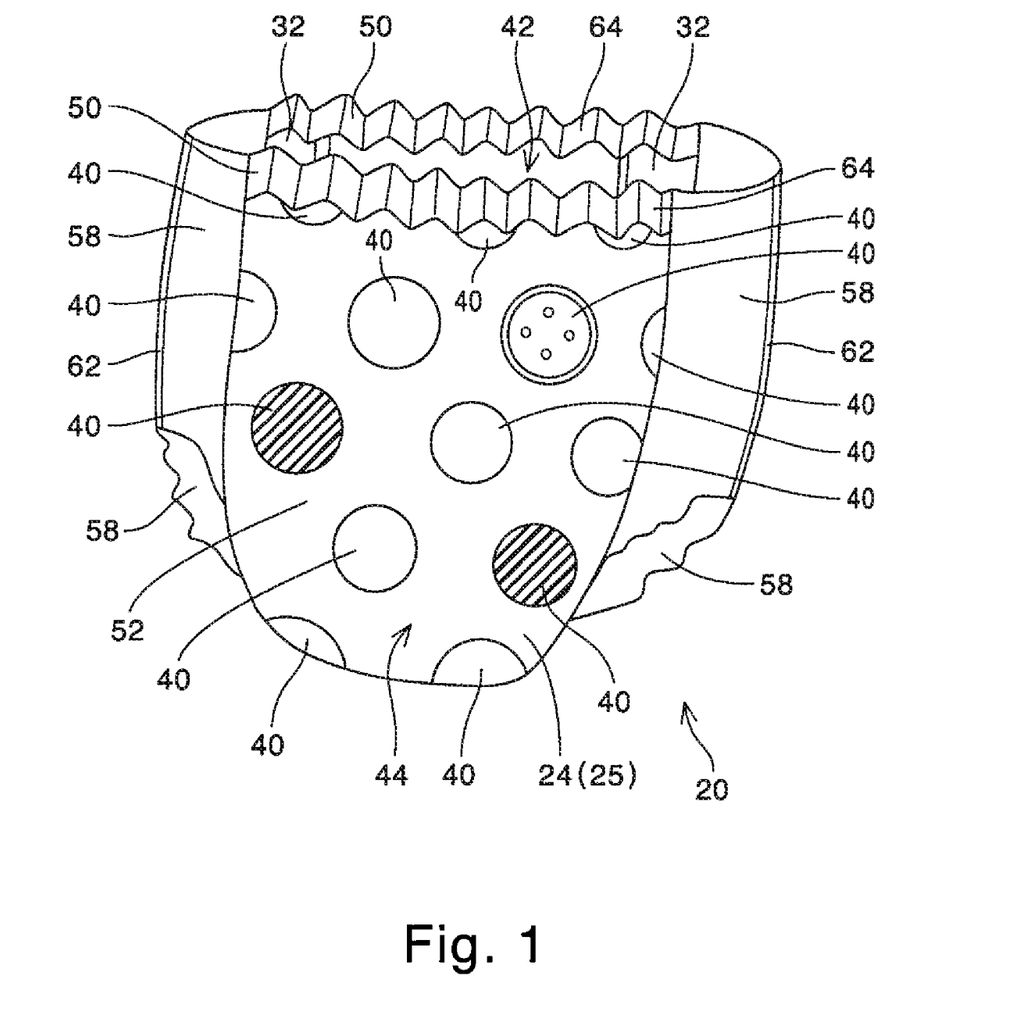
FIG. 1 illustrates a perspective front view of an absorbent article comprising a graphic.
Figure 2:
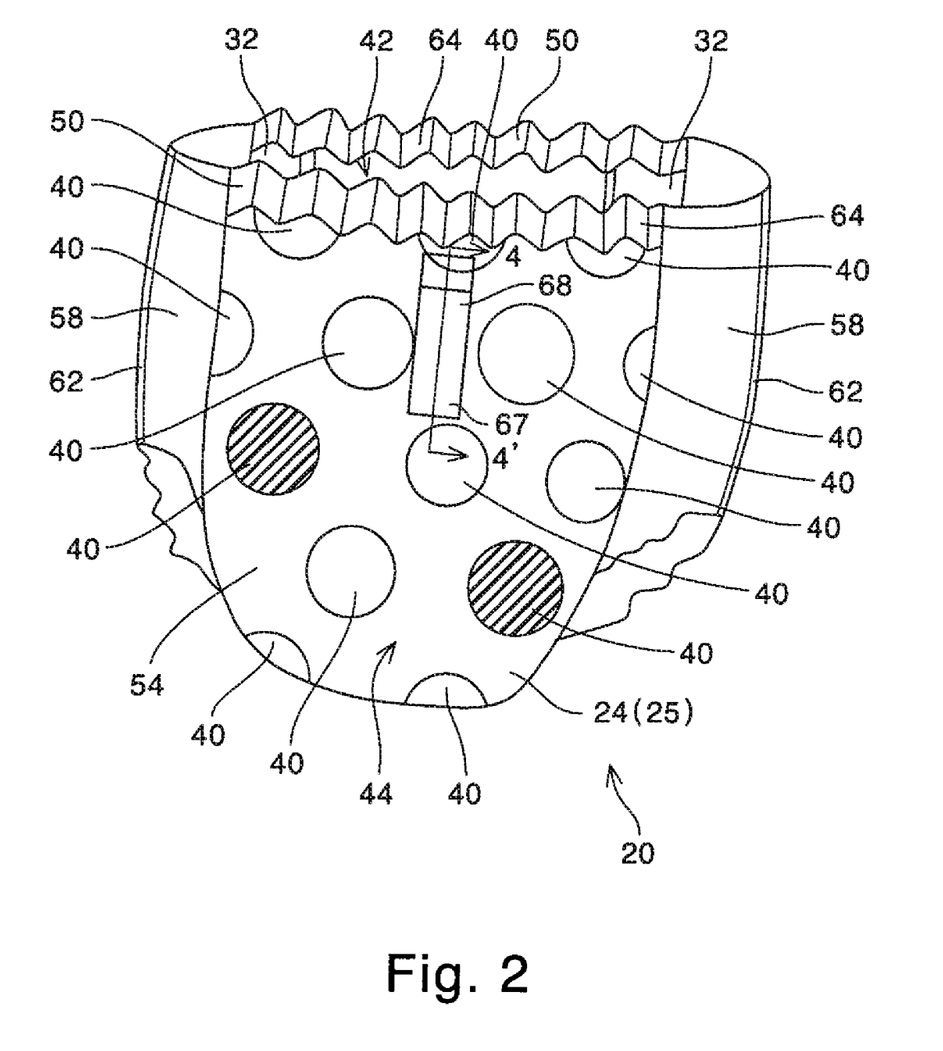
FIG. 2 illustrates a perspective rear view of the absorbent article of FIG. 1.
Figure 3:
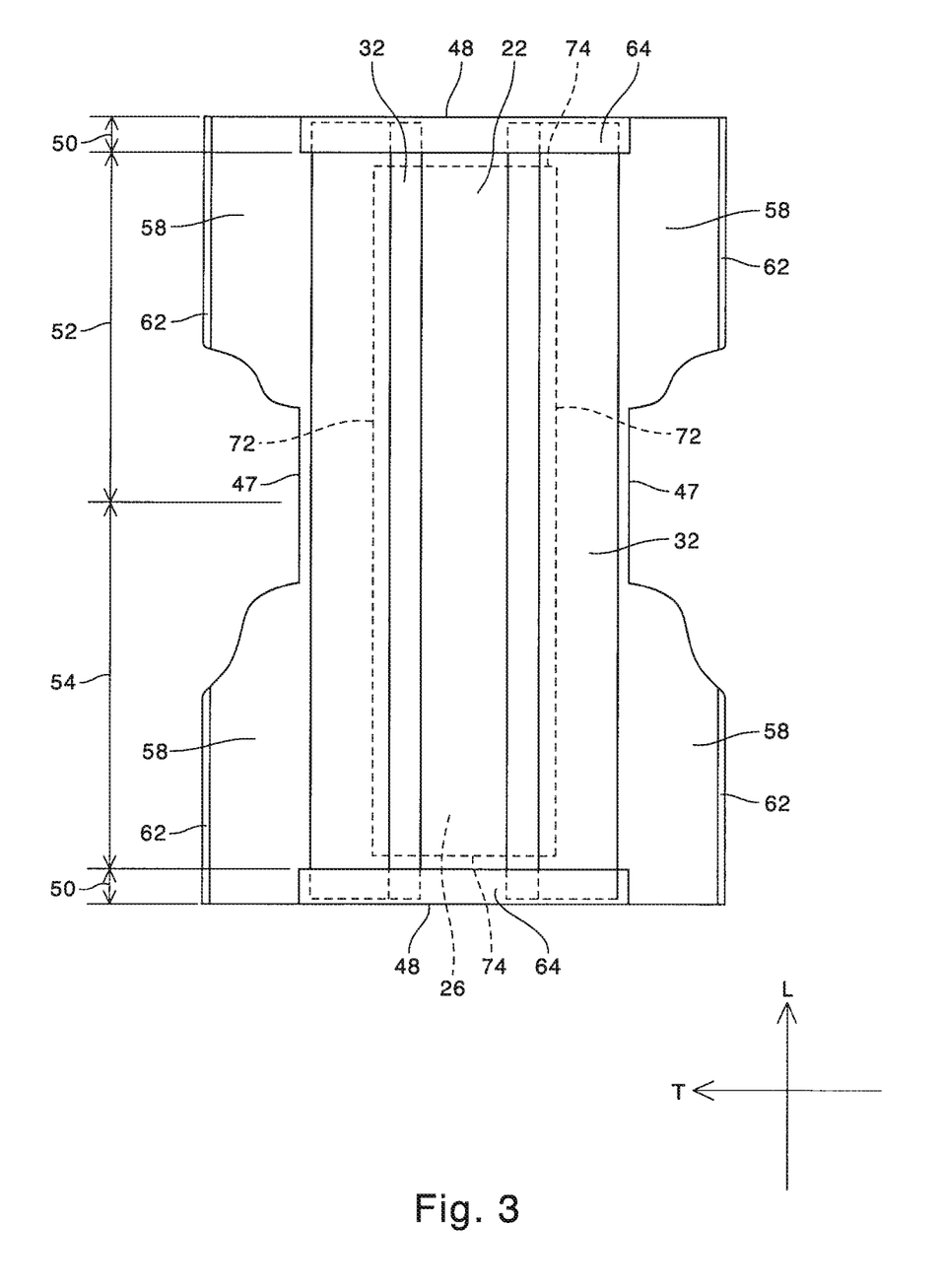
FIG. 3 illustrates an expansion view of the disposable absorbent article of FIGS. 1 and 2 whose side seams are detached.

FIGS. 1, 2 and 3 illustrate a disposable pull-on diaper which is representative of a disposable absorbent article to be contained in a package. The diaper 20 comprises a liquid permeable topsheet 22, a liquid impermeable backsheet 24 attached to the topsheet 22 and an absorbent core 26 disposed between the topsheet 22 and the backsheet 24. The diaper 20 has a body facing surface 42 and an external surface 44 opposed to the body facing surface 42. The diaper 20 comprises a leg cuff 32 disposed on the body facing surface 42 of the diaper 20.

Referring to FIG. 3, the diaper 20 extends in a longitudinal direction L and in a transverse direction T. "Longitudinal" refers to a line, axis or direction in the plane of the diaper 20 that is generally aligned with (e.g., approximately parallel to) a vertical plane which bisects a standing wearer into left and right body halves when the diaper 20 is worn. "Transverse" or "lateral", are interchangeable, and refer to a line, axis or direction which lies within the plane of the diaper 20 that is generally perpendicular to the longitudinal direction L. The diaper 20 comprises a pair of longitudinal side edges 47 and a pair of transverse end edges 48. The diaper 20 comprises a pair of waist regions 50, a front region 52, a rear region 54 and a pair of elastic side regions 58 which connect the front region 52 and the rear region 54. Each of the elastic side regions 58 is formed from two separate elastic portions and they are joined together to form side seams 62.

The topsheet 22 may be compliant, soft feeling, and non-irritating to the wearer's skin. The topsheet 22 is liquid permeable or pervious, permitting discharged materials to readily penetrate through its thickness. A liquid permeable topsheet 22 may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. When the topsheet 22 includes a nonwoven web, the web may be manufactured by a wide number of known techniques. For example, the web may be spunbonded, carded, wet-laid, melt-blown, hydroentangled, combinations of the above, or the like. The body facing surface of the topsheet 22 can be made hydrophilic by the treatment with a surfactant. The external surface of the topsheet 22 may be attached to the absorbent core 26.

The backsheet 24 may be impervious to discharged materials and may be manufactured from a thin plastic film, and other flexible liquid impervious materials may be also used. The backsheet 24 prevents discharged materials absorbed and contained in the absorbent core 26 from leaking out of the absorbent article 20. The backsheet 24 may thus include woven or nonwoven materials, polymeric films such as thermoplastic films of polyethylene or polypropylene, or composite materials such as a film-coated nonwoven material. The backsheet 24 may include a single layer material, or a plurality of layer materials. In one embodiment, the backsheet 24 may be a single layer polyethylene film. The backsheet 24 may have a microporous structure which can permit vapors to escape from the absorbent core (called "breathable backsheet") while still preventing discharged materials from passing through the backsheet 24.

The backsheet 24 may be further covered by nonwoven 25. In the embodiment of FIGS. 1 and 2, the nonwoven 25 covers the external surface of the backsheet 24. The nonwoven 25 may make the diaper 20 feel soft. The nonwoven 25 has a loose texture in general, and an object looks blurred when it is covered by the nonwoven 25.

The absorbent core 26 is capable of receiving, absorbing and/or retaining discharged materials from the body. The absorbent core 26 may be compressible, conformable and non-irritating to the wearer's skin. The absorbent core 26 has a pair of longitudinal side edges 72 and a pair of transverse end edges 74. The absorbent core 26 may be formed by a single layer material or a plurality of layer materials. The absorbent core 26 may include any of a wide variety of liquid-absorbent materials known in the art, such as comminuted wood pulp, which is generally referred to as airfelt. The absorbent core 26 may comprise a multi-bonded air laid nonwoven material. The absorbent core 26 may be manufactured in a wide variety of sizes and shapes. The absorbent core 26 thus can take any shape in its top plan view. Shapes for the absorbent core 26 may include an oval, a rectangle, an hourglass, a circle, a square, and any other shape. In the embodiment of FIG. 3, the core 26 takes a rectangle shape.

Referring to FIGS. 1, 2 and 3, the diaper 20 comprises a pair of elastic waist bands 64 in the waist regions 50. The elastic waist bands 64 are disposed longitudinally outside the transverse ends 74 of the absorbent core 26. The elastic waist bands 64 provide the waist regions 50 with elasticity.

Referring to FIGS. 1, 2 and 3, the diaper 20 further comprises a pair of leg cuffs 32 for providing improved containment of discharged materials. Each leg cuff 32 may comprise several different embodiments for blocking or reducing the leakage of discharged materials in the leg regions on the body facing surface 42 of the diaper 20. The leg cuff 32 extends in a substantially longitudinal direction L to overlap the elastic waist bands 64 in order to block or reduce leakage of discharged materials from the diaper 20. In the embodiment of FIG. 3, the leg cuff 32 is secured to the topsheet 22. Additionally or alternatively, the leg cuff 32 may be secured to the backsheet 24 and/or the nonwoven 25. The material for the leg cuff 32 may be repellent nonwoven. The leg cuff 32 may be breathable and liquid impervious.

The diaper 20 comprises a graphic 40 which is visible from outside. The graphic 40 may be disposed in the waist region 50, the front region 52, the rear region 54, and/or the side region 58 of the diaper 20. In order to draw consumers' attention, the graphic 40 may be disposed in the front region 52 and the rear region 54. The graphic 40 may extend from the front region 52 to the rear region 54 as a continuous graphic. Referring to FIG. 1, the diaper 20 comprises a plurality of polka dot graphics 40 printed on the external surface of the front region 52. Also referring to FIG. 2, the diaper 20 comprises a graphic 40 printed on the external surface of the rear region 54, said graphic 40 extending from the front region 52 of FIG. 1. The term "graphic" may refer, but is not limited, to an image, a design, a pattern, symbology, indicia, or the like. "Graphic" includes, for example, animals (e.g., dogs, cats, bears, squirrels, tigers, lions, mice, foxes, and the like); birds (e.g., swallows, sparrows, hawks, ducks, eagles, swans, and the like); human beings; plants such as flowers (e.g., dandelions, roses, tulips, cherry blossoms, sunflowers, carnations, and the like), trees and leaves; stars; moons; cartoon characters; toys (e.g., dolls, bats, balls, rackets, and the like); electric instruments (e.g., mobile phones, computers, and the like); ornaments (e.g., frills, ribbons, buttons, belts, neckties, caps, hats, and the like); garment-like patterns (e.g., denims, borders, stripes, checks, polka dots, and the like); seasonal things or goods such as a snowman; landscapes; and the like. The graphic 40 may be printed on a part of the backsheet 24 or on the substantially whole surface of the backsheet 24. The graphic 40 may be printed on the body facing surface of the backsheet 24. In the embodiment of FIG. 1, the graphic 40 is printed on the backsheet film, and the backsheet film is further covered by the nonwoven 25. Therefore, the graphic 40 looks blurred when it is covered by the nonwoven 25 and the diaper 20 comprising such a graphic 40 looks noble and refined. The graphic 40 may be printed on the nonwoven 25. The graphic 40 may be printed on another material than the backsheet 24 or the nonwoven 25 (e.g. a polymeric film, a sheet of paper, and the like) and the printed material may be joined to the backsheet 24 or the nonwoven 25. The graphic 40 can be printed by any conventional printing methods or technologies known in the art, including, but not limited to, a gravure printing, a flexo printing, an offset printing, an ink jet printing, and the like.

Figure 4:
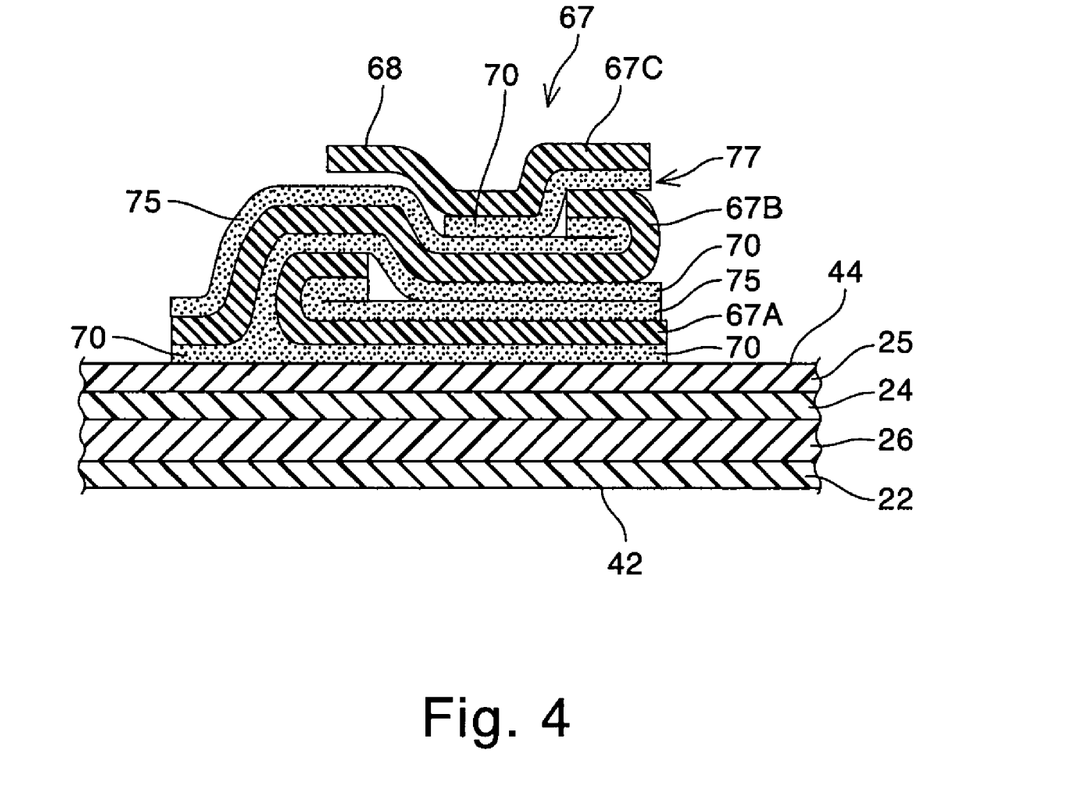
FIG. 4 illustrates a cross sectional view of the disposable tape of FIG. 2 taken along by 4-4' line.

Referring to FIG. 2, the absorbent article 20 comprises a disposable tape 67 secured to the external surface 44 of the rear region 54 of the diaper 20. FIG. 4 illustrates a partial cross sectional view of the absorbent article of FIG. 2 along 4-4' line. The sectional view illustrates the structure of the disposable tape 67. The disposable tape 67 is used to secure a soiled diaper containing discharged materials for disposal. The disposable tape 67 may be secured to the front region 52 or the rear region 54 of the absorbent article 20. In the embodiment of FIG. 2, the pull-on diaper 20 comprises a disposable tape 67 secured to the external surface 44 in the rear region 54 of the diaper 20. The disposable tape 67 is used to fasten the used diaper containing the discharged materials and thus soiled diaper is folded down to wrap the discharged materials. The disposable tape 67 comprises a disposable tape adhesive 70.

Referring to FIG. 4, the disposable tape 67 comprises a first section 67A, a second section 67B and a third section 67C. The first section 67A is secured by a disposable tape adhesive 70 to the nonwoven 25, and is secured by a disposable tape adhesive 70 to the second section 67B at a first adhesion portion 76. The second section 67B is secured by a disposable tape adhesive 70 to the third section 67C at a second adhesion portion 77. The first section 67A may have a release agent 75 on the surface facing the second section 67B. The second section 67B may also have a release agent 75 on the surface facing the third section 67C. For example, a suitable release agent 75 can be a coating of silicon or a release liner made of polyethylene. Overall, the three sections of the disposable tape 67A, 67B and 67C compose a Z-folding on the external surface of the nonwoven 25.

The third section 67C comprises a disposable tape tab 68 on the opposite end to the second adhesion portion 77. The user can pull the disposable tape tab 68 to unfold the disposable tape 67 for disposal. When the disposable tape tab 68 is pulled, the first section 67A is partially detached from the second section 67B. Similarly, the second section 67B is partially detached from the third section 67C. Nevertheless, the three sections 67A, 67B and 67C are partially secured to each other with the disposable tape adhesive 70 at the first adhesion portion 76 and at the second adhesion portion 77. Therefore, when the disposable tape tab 68 is pulled, the three sections 67A, 67B and 67C compose a long disposable tape which can roll a soiled diaper. The soiled diaper is rolled up to conceal the discharged materials inside and the rolled up configuration of the soiled diaper is fixed with the disposable tape 67. The material used for the disposable tape 67 illustrated in FIGS. 2 and 4 is a polypropylene film.

The disposable tape adhesive 70 may be used to secure the disposable tape 67 to the diaper 20. The disposable tape 67 may be secured to the nonwoven 25 not to be easily detached when the diaper 20 is worn. The disposable tape adhesive 70 may also be used to attach two portions of the disposable tape 67 such as the first section 67A and the second section 67B, or the second section 67B and the third section 67C not to be easily detached when the diaper 20 is worn. The adhesibility of the disposable tape adhesive 70 may be strong enough to keep the disposable tape 67 secured to the nonwoven 25 when the disposable tape tab 68 is pulled. The nonwoven 25 has a relatively rough surface and therefore the disposable tape adhesive 70 may have a basis weight of not less than about 20 $g/m^2$ to secure the disposable tape 67 to the nonwoven 25 firmly. The adhesibility of the disposable tape adhesive 70 may be strong enough to keep the first section 67A secured to the second section 67B at the first adhesion portion 76 and to keep the second section 67B secured to the third section 67C at the second adhesion portion 77 when the disposable tape tab 68 is pulled. The basis weight of the disposable tape adhesive 70 can be not less than about 25 $g/m^2$. The basis weight of the disposable tape adhesive 70 may be not more than about 150 $g/m^2$.

Materials used for the disposable tape 67 may include, but are not limited to, polymeric film, such as polypropylene films, polyethylene films, co-extruded polyethylene and ethylene vinyl acetate films and the like. The material for the disposable tape may be of biodegradable, recyclable, non-biodegradable or non-recyclable materials. In the embodiment of FIGS. 2 and 4, the disposable tape is polypropylene.

Figure 5:
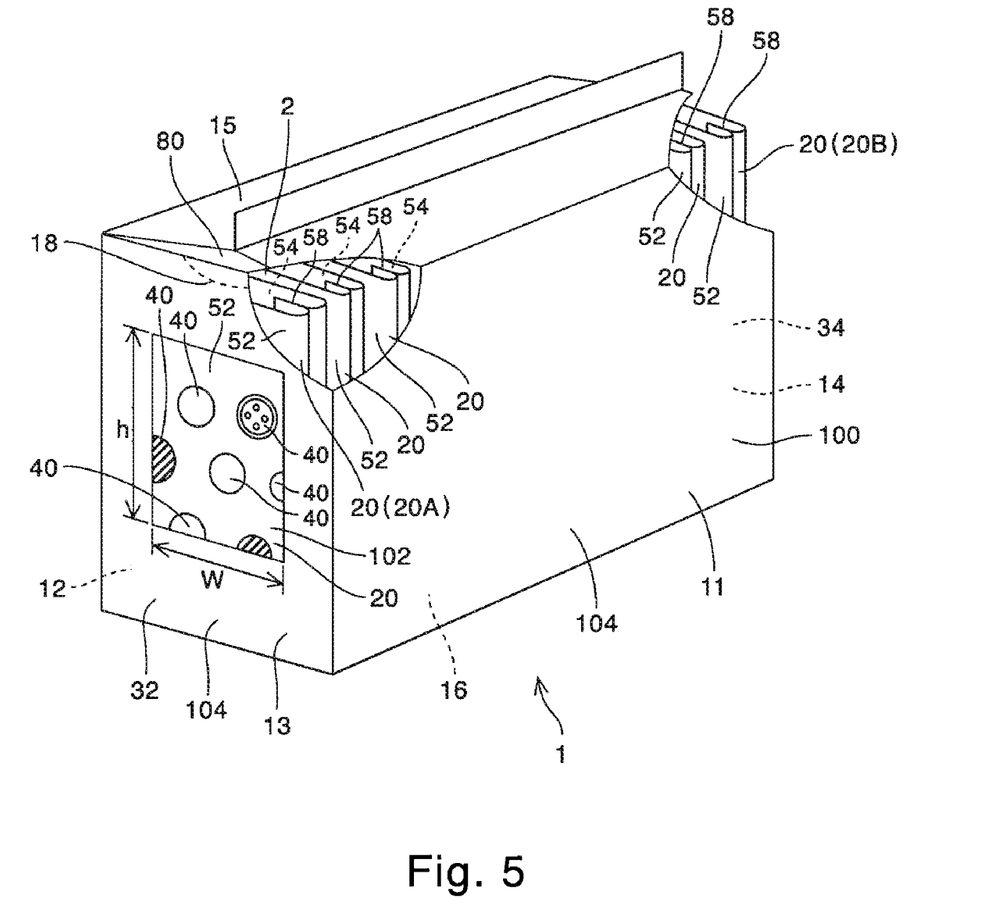
FIG. 5 illustrates a perspective view of an absorbent product comprising the absorbent article contained in a package.

Disposable tape adhesives may be selected from pressure sensitive adhesives, non-pressure sensitive adhesives, hot melt adhesives, and the like. Any adhesive materials known in the art can be used for the disposable tape adhesive such as SIS (styrene-isoprene-styrene block copolymer), SBS (styrene-butadiene-styrene block copolymer), polyolefin, and the like. For example, the following adhesives may be used; Findley H2401 (SIS Polymer), Findley H2861 (SIS Polymer), Fuller 3166 (Polyolefin), and NSC 519 (SBS Polymer). FIG. 5 illustrates a perspective view of an absorbent product comprising a package and a plurality of disposable absorbent articles therein. The package 100 may be any shape known in the art. In the embodiment of FIG. 5, the package 100 has a polyhedral shape defining or forming a polyhedral enclosure. The package 100 has a shape of a parallelepiped including a front panel 11, a rear panel 12 opposed to the front panel 11, a left side panel 13, a right side panel 14 opposed to the left side panel 13, a top panel 15 which connects the front panel 11, the rear panel 12, the left side panel 13 and the right side panel 14, and a bottom panel 16 opposed to the top panel 15.

The package 100 containing a plurality of absorbent articles 20 may include those constructed as cartons and/or flexible packages, such as pouches and bags. The package 100 may be formed by any suitable material and can take any structure known in the art. Materials used to construct packages may include, but are not limited to, polymeric film, such as polypropylene films, polyethylene films, co-extruded polyethylene and ethylene vinyl acetate films and the like, paperboard and coated paper. The package material may be of biodegradable, recyclable, non-biodegradable or non-recyclable materials. In the embodiment of FIG. 5, the package 100 is a flexible bag which is formed by a thin film material. The package 100 may be formed through manipulation of a single sheet of material, such as folding, by attaching multiple sheets to one another or a combination thereof. The package 100 may be sealed or adhered by means known in the art, such as heat seal, ultrasonics, adhesives, hook and loop fasteners and the like. A film material for the package 100 illustrated in FIG. 5 is a polyethylene film.

An opening device for retrieving absorbent articles 20 may be provided at an arbitrary area of the package 100. In the embodiment of FIG. 5, an opening device 18 for retrieving diapers 20 is provided on the left side panel 13. The opening device 18 may have an enough size (e.g., the length) so that the diapers 20 can be retrieved easily by the user. The opening device 18 can take any structure, shape and dimension known in the art. The opening device 18 may include a line of weakness which extends within the left side panel 13. The line of weakness may include a line of perforation formed in the left side panel 13. The line of weakness may extend into the other panels such as the top panel 15 and/or the bottom panel 16, from the left side panel 13. The two side portions of the package 100 are closed by forming a top gusset structure 80 which is formed by sealing the material film.

The package 100 comprises a first panel 32 and a second panel 34 opposed to the first panel 32. The first panel 32 comprises a first window area 102. The first panel 32 comprising the first window area 102 may be disposed on any place of the package 100, for example, on the front panel 11, the rear panel 12, the left side panel 13, the right side panel 14, the top panel 15 or the bottom panel 16. In the embodiment of FIG. 5, the left side panel 13 is the first panel 32 which comprises the first window area 102, and the right side panel 14 opposed to the left side panel 13 is the second panel 34. Alternatively, the front panel 11 may be the first panel 32 and the rear panel 12 opposed to the front panel 11 may be the second panel 34. The top panel 15 may be the first panel 32 and the bottom panel 16 opposed to the top panel 15 may be the second panel 34.

The first panel 32 comprises the first window area 102 (refer to FIG. 5). The first window area 102 may serve as a "communication window" for the customers to perceive the graphic 40 in the front region 52 disposed on the diaper 20 contained in the package 100. The first window area 102 allows light transmittance so that the graphic 40 of the front region 52 may be visible through the first window area 102. The first panel 32 may further comprise an ultraviolet barrier area 104. The "ultraviolet barrier area" refers to an area of the surface of the package 100 which blocks or reduces the ultraviolet transmittance. The first window area 102 allows more light transmittance than the ultraviolet barrier area 104. The ultraviolet barrier area 104 allows less ultraviolet transmittance than the first window area 102. In one embodiment, the first window area 102 may occupy the whole area of the first panel 32 to provide a large view of the graphic 40 in the front region 52. In the embodiment of FIG. 5, the first window area 102 is surrounded by the ultraviolet barrier area 104.

Figure 6:
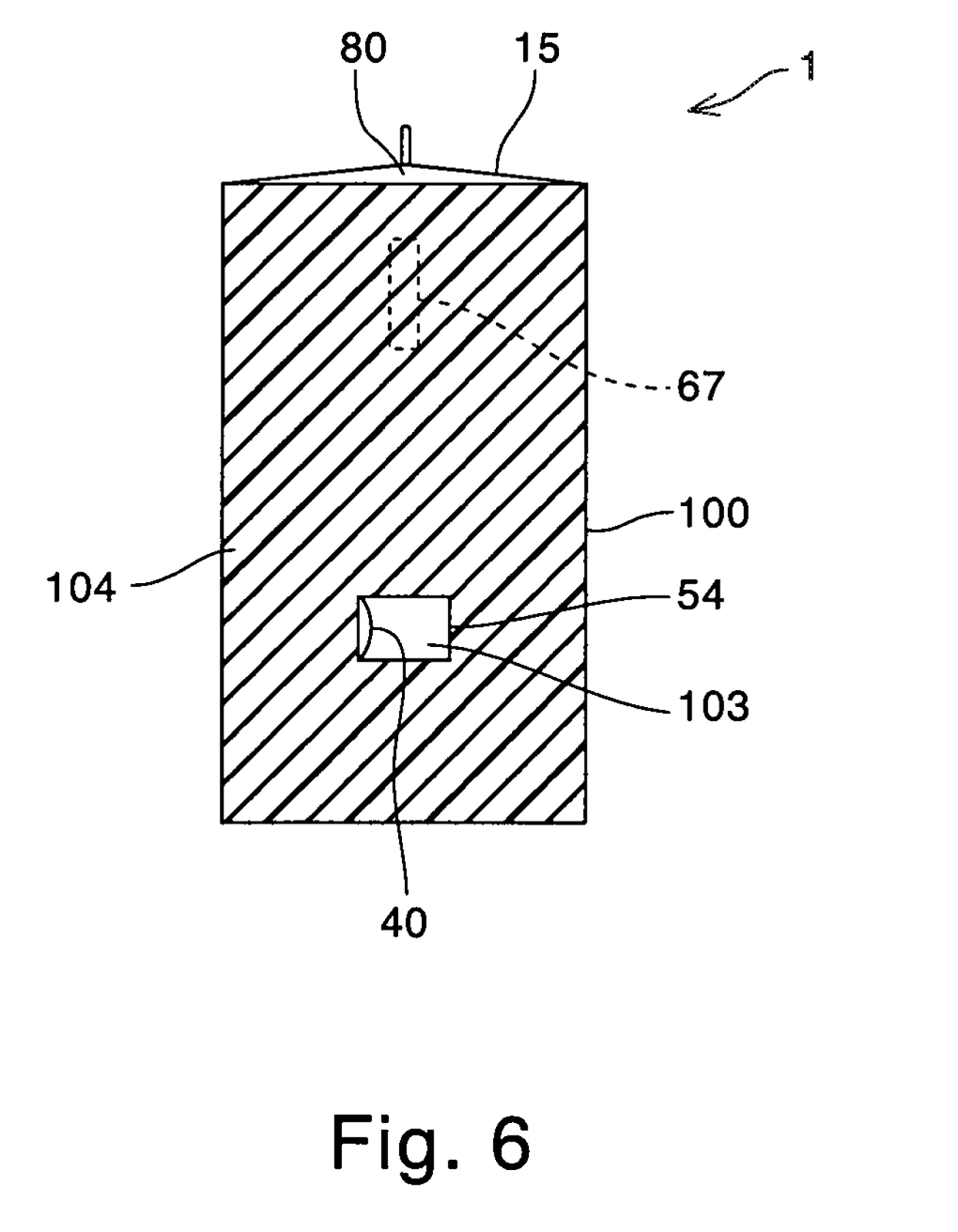
FIG. 6 illustrates a side view of the absorbent product of FIG. 5 seen from the second panel.
Figure 7:
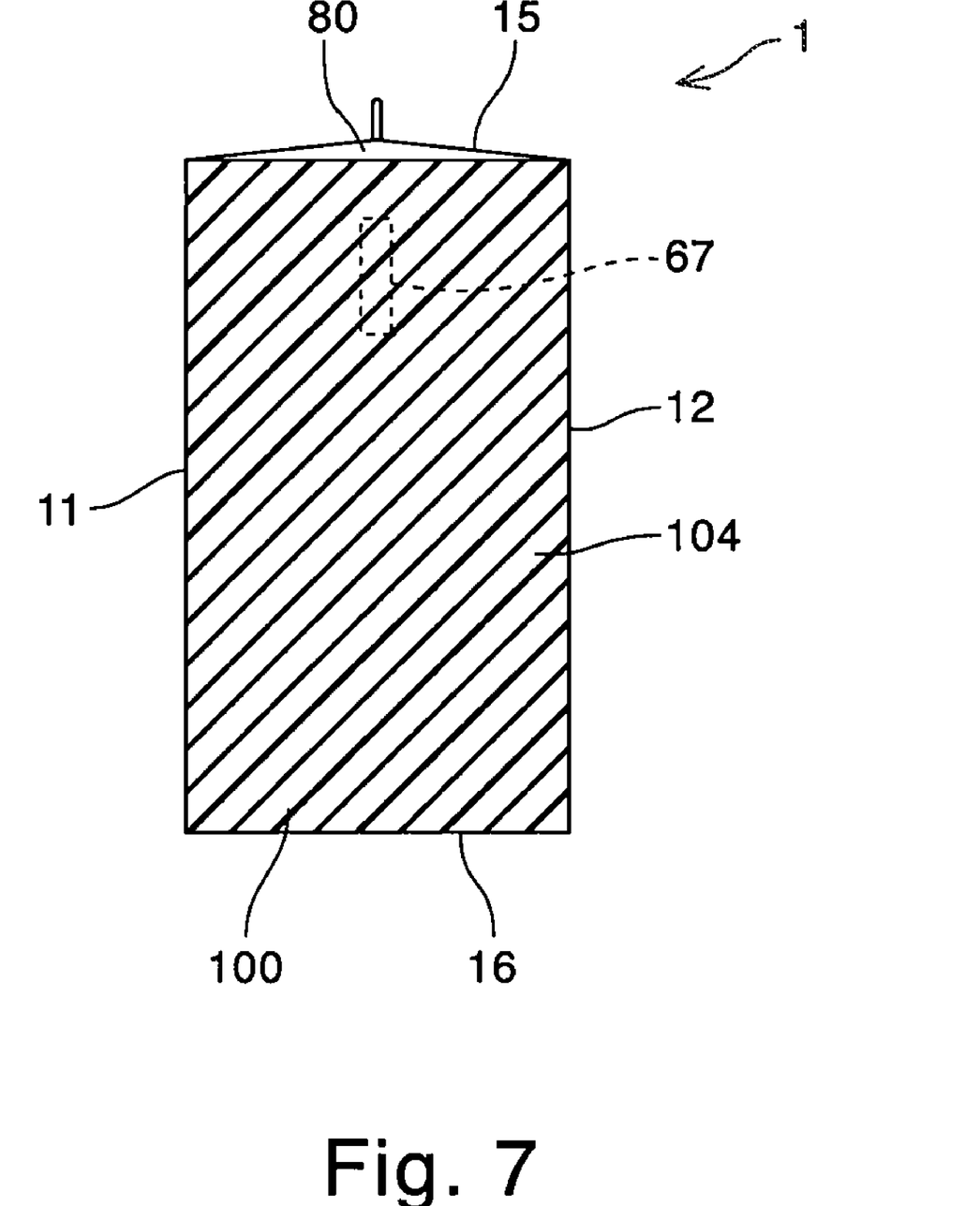
FIG. 7 illustrates another embodiment of a side view of the absorbent product of FIG. 5 seen from the second panel.
Figure 8:
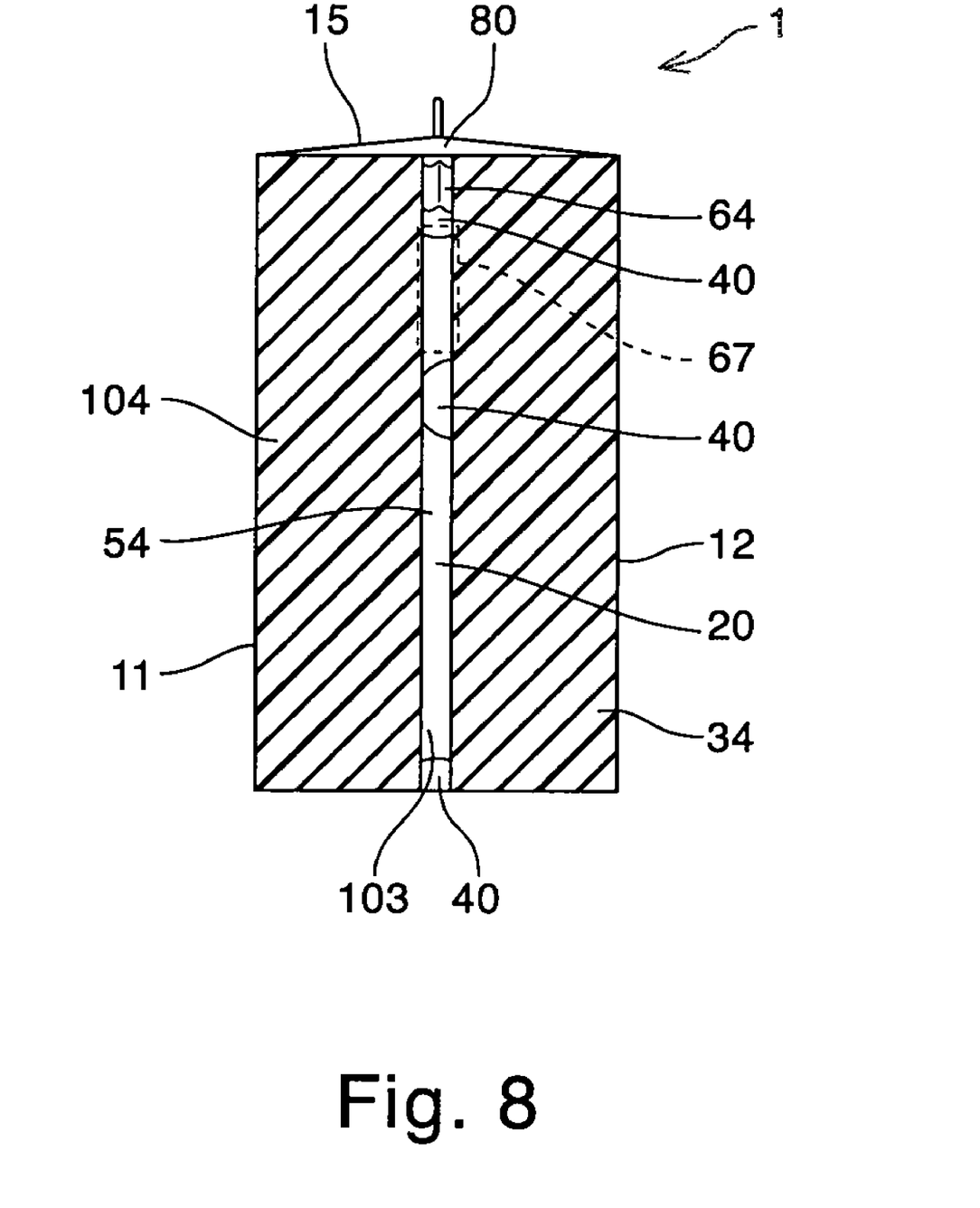
FIG. 8 illustrates still another embodiment of a side view of the absorbent product of FIG. 5 seen from the second panel.
Figure 9:
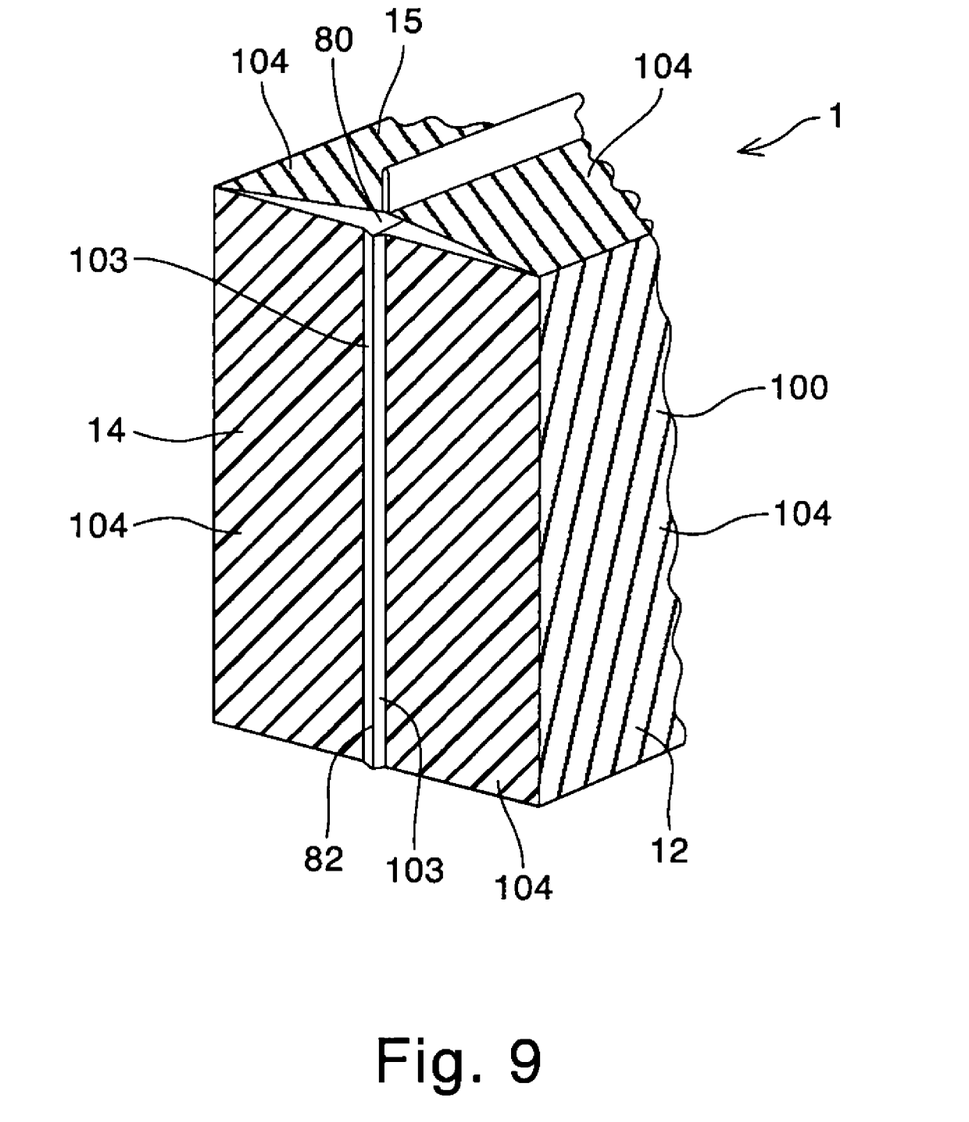
FIG. 9 illustrates one embodiment of a perspective partial view of the absorbent product to show a sealing line of the second panel.

The second panel 34 may comprise a second window area 103 (refer to FIGS. 6 and 8) or may comprise no window area (refer to FIG. 7). When the second panel 34 comprises the second window area 103, the second window area 103 may be surrounded by the ultraviolet barrier area 104 in the second panel 34. The second window area 103 may allow light transmittance. The second window area 103 allows more light transmittance than the ultraviolet barrier area 104. The ultraviolet barrier area 104 allows less ultraviolet transmittance than the second window area 103. FIGS. 6, 7 and 8 illustrate embodiments of the second panel 34. In the embodiment of FIG. 6, the second panel 34 comprises the second window area 103 which is smaller than the first window area 102 as illustrated in FIG. 5 and the second window area 103 is surrounded by the ultraviolet barrier area 104. In the embodiment of FIG. 7, the second panel 34 consists of the ultraviolet barrier area 104 and comprises no window area. As the second panel 34 comprises no window area, the graphic of the rear region 54 of the diaper 20 may be substantially invisible. In the embodiment of FIG. 8, the second panel 34 comprises the second window area 103 having an elongated shape in the center region 112 of the second panel 34. The second window area 103 may be made in a portion of the second panel 34 where the two portions of the polyethylene films forming the package 100 are attached to form a sealing line 82 (refer to FIG. 9). The area including the sealing line 82 may not be coated by a colorant so that the two pieces attach to each other easily. The width of the second window area 103 of FIG. 8 may not be so large that the graphic 40 inside the package 100 is substantially visible from outside. Therefore, the second window 103 illustrated in FIG. 8 may not serve as a communication window like a first window area 102. The disposable tape 67 disposed in the rear region 54 of the diaper 20 may be covered by the ultraviolet barrier area 104 of the second panel 34 (refer to FIGS. 6 and 7). Alternatively, the disposable tape 67 of the diaper 20 may be visible through the second window area 103 (refer to FIG. 8). Similarly, the first panel 32 may comprise the area including the sealing line 82.

The first window area 102 and the second window area 103 (collectively referred to as "window area" hereafter) may be transparent or translucent to allow the graphic 40 of the diaper 20 to be visible therethrough. In the embodiment of FIGS. 5, 6 and 8, the first window area 102 and the second window area 103 are transparent and the ultraviolet barrier area 104 is opaque. In another embodiment, the window area may be translucent and the ultraviolet barrier area may be opaque. In still another embodiment, the window area may be transparent and the ultraviolet barrier area may be translucent. The light transmittance and the ultraviolet transmittance are distinguished between these two areas. Otherwise, both the window area and the ultraviolet barrier area may be translucent and these two areas are distinguished by differentiating the light transmittance and ultraviolet transmittance from each other. The ultraviolet barrier area may be distinguished from the window area by the color difference. For example, the ultraviolet barrier area may have a strong color which blocks or reduces light transmittance and ultraviolet transmittance and the window area may have a light color which allows more light transmittance and ultraviolet transmittance than the ultraviolet barrier area.

The window area and the ultraviolet barrier area can be formed by any means known in the art. A window area may be prepared by using a transparent or translucent material known in the art (e.g., a polymeric film such as thermoplastic film of polyethylene or polypropylene, or a composite material such as a film-coated nonwoven material) as it is or by coloring the material. An ultraviolet barrier area may be prepared by coloring the transparent or translucent material to have less light transmittance and less ultraviolet transmittance. The transparent or translucent material may be partially colored, for example by printing. In one embodiment, the transparent or translucent material may be partially printed and the rest of the material is left unprinted. The printed area may be an ultraviolet barrier area and the unprinted area may be a window area. In another embodiment, substantially the whole area of the transparent or translucent material may be printed to provide a translucent area and an opaque area. In such a case, the transparent or translucent material may be partially printed to be translucent to correspond to the window area and the rest of the material may be printed to be opaque to correspond to the ultraviolet barrier area. The material can be printed by any conventional printing methods or technologies known in the art, including, but not limited to, a gravure printing, a flexo printing, an offset printing, an ink jet printing, and the like.

The window area can take any shape such as a circle, a square, a rectangle, a trapezoid, an ellipse, a triangle, an oval, a semi-circle, a sector, a star or any other shape. The shape of the first window area 102 illustrated in FIG. 5 is a rectangle. The shape of the second window area 103 illustrated in FIG. 6 is also a rectangle. The shape of the second window area 103 illustrated in FIG. 8 is an elongated rectangle. The window area can have any sizes or dimensions (e.g., the length and the width for a rectangular window, the diameter for a circle window). In the embodiment of FIG. 5, the first window area 102 is smaller than the first panel 32. The width W of the first window area 102 may be between about 40 mm and about 100 mm and the height H of the first window area 102 may be between about 40 mm and about 200 mm. The first window area 102 may occupy between about 30% and about 100% of the total area of the first panel 32. The second window area 102 may occupy between about 0% and about 50% of the total area of the second panel 34 as far as the graphic 40 in the front region 52 is more visible than the graphic 40 in the rear region 54. In the embodiment of FIG. 8, the second window area 103 occupies a narrow area in the second panel 34.

The ultraviolet barrier area 104 may be additionally or alternatively protected by an ultraviolet absorbing agent. Examples of commercially available ultraviolet absorbing agents include, for example, benzophenone type (Viosorb 110, Viosorb 130, EVERSORB 10, EVERSORB 11, EVERSORB 12), benzotriazole type (Viosorb 520, Viosorb 550, Viosorb 582, Viosorb 583, Viosorb 590, Viosorb 591, EVERSORB 70, EVERSORB 71, EVERSORB 72, EVERSORB 73, EVERSORB 74, EVERSORB 75, EVERSORB 76, EVERSORB 234, EVERSORB 78, EVERSORB 80, EVERSORB 81, Tinuvin 213, Tinuvin 234, Adekastab LA-31), hindered amine light stabilizer (HALS) (Sanol LS-770, Sanol LS-765, Tinuvin 622, Chimassorb 944, Cyassorb UV-3346, Adekastab LA-57, Chimassorb 119, EVERSORB 90, EVERSORB 91, EVERSORB 93, EVERSORB S02), benzoate type (Viosorb 80, SB-UVA 612) and the like.

The light transmittance ranges may provide an effective view of the graphic 40 through the window area. The light transmittance of the window area may be between about 15% and about 100%, or between about 25% and about 100%. The window area may have more than about 20% greater light transmittance than the ultraviolet barrier area. A method for measuring the light transmittance will be described in the "Test Methods" section. The light transmittance of the ultraviolet barrier area may be between about 0% and about 70% or between about 0% and about 50% insofar as the window area allows more light transmittance than the ultraviolet barrier area. Lower light transmittance can serve to provide lower ultraviolet transmittance.

The ultraviolet transmittance ranges may provide an effective protection of the disposable tape adhesive 70 from the ultraviolet ray. The disposable tape adhesive 70 may have a basis weight of not less than about 10 g/m². The ultraviolet transmittance of the ultraviolet barrier area may be between about 0% and about 50%. Or the ultraviolet transmittance of the ultraviolet barrier area may be between about 0% and about 25%. The ultraviolet barrier area may have less than about 20% lower ultraviolet transmittance than the window area. A method for measuring the ultraviolet transmittance will be described in the "Test Methods" section. The ultraviolet transmittance of the window area may be between about 15% and about 100% insofar as the ultraviolet barrier area allows less ultraviolet transmittance than the window area. Or the ultraviolet transmittance of the ultraviolet barrier area may be between about 25% and about 100%. As is easily understood by a person skilled in the art, the lower ultraviolet transmittance means the higher ultraviolet blockade.

The graphic 40 in the front region 52 facing the first panel 32 is more visible than the graphic 40 in the rear region 54 facing the second panel 34 when a plurality of absorbent articles 20 contained in the package 100 are viewed from outside. As the graphic 40 in the first region 52 is more visible than the graphic 40 in the rear region 54, the retailers may be motivated to display the absorbent product 1 so that the side of the first panel 32 may face toward the customers.

In order that the graphic 40 in the front region 52 may be more visible than the graphic 40 in the rear region 54, the first window area 102 may be larger than the second window area 103 (refer to FIGS. 5 and 6). In one embodiment, the graphic 40 in the first region 52 may be substantially wholly visible through the first window area 102, while the graphic 40 in the rear region 54 may be only partially visible through the second window area 103. The first window area 102 may be at least about 20%, about 30% or about 50% larger than the second window area 103 so that a person may easily notice that the first window area 102 is obviously larger than the second window area 103.

Alternatively or additionally, the first window area 102 may have more light transmittance than the second window area 103 in order that the graphic 40 in the front region 52 may be more visible than the graphic 40 in the rear region 54. The light transmittance of the first window area 102 may be at least about 20%, about 30% or about 50% more than that of the second window area 103 so that a person may easily notice that the first window area 102 has obviously more transparency than the second window area 103. When the first window area 102 has more light transmittance than the second window area 103, the first window area 102 may be substantially as large as the second window area 103. The first window area 102 may be larger than the second window area 103 in addition to having more light transmittance than the second window area 103.

The absorbent product 1 comprises a package 100 and a plurality of absorbent articles 20 in the package 100. The package 100 defines an interior space 2 for containing a plurality of absorbent articles 20. The graphic 40 of each absorbent article 20 may be identical with that of another absorbent article 20 or may be different from that of another absorbent article 20. In the embodiment of FIG. 5, a plurality of diapers 20 are compressed to form one stack within the interior space 2 of the package 100.

In the embodiment of FIGS. 5 and 6, a plurality of diapers 20 are stacked so that the front region 52 of one diaper 20 and the rear region 54 of its adjacent diaper 20 may face each other. A plurality of the diapers 20 may be stacked in a way that the disposable tapes 67 attached to the rear region 54 face the same orientation. When the plurality of diapers 20 are stacked in a way that all the disposable tapes 67 face the same orientation, the front region 52 may face the first panel 32 and the rear region 54 may face the second panel 34. The diaper 20 may be folded so that the side regions 58 may be at least partially hidden between the front region 52 and the rear region 54.

"Visible" may mean that the graphic feature is perceivable by a viewer. The visibility of the graphic through the window area may be subject to the position, the size and/or the range of the graphic and the window. For example, when the window area is disposed in the relatively peripheral region of the panel, the window area may not allow the graphic to be visible. When the window area is disposed in the relatively central region of the panel, the viewer may be able to perceive the window area easily. For example, when the window area is large enough, the window area may allow the graphic to be visible. And when the whole graphic is visible through the window area, the window area may allow the graphic to be visible even if the window area is rather small.

The term "graphic feature" may include, for example, a primary element of the graphic, a design element of the graphic and the like.

Figure 10:
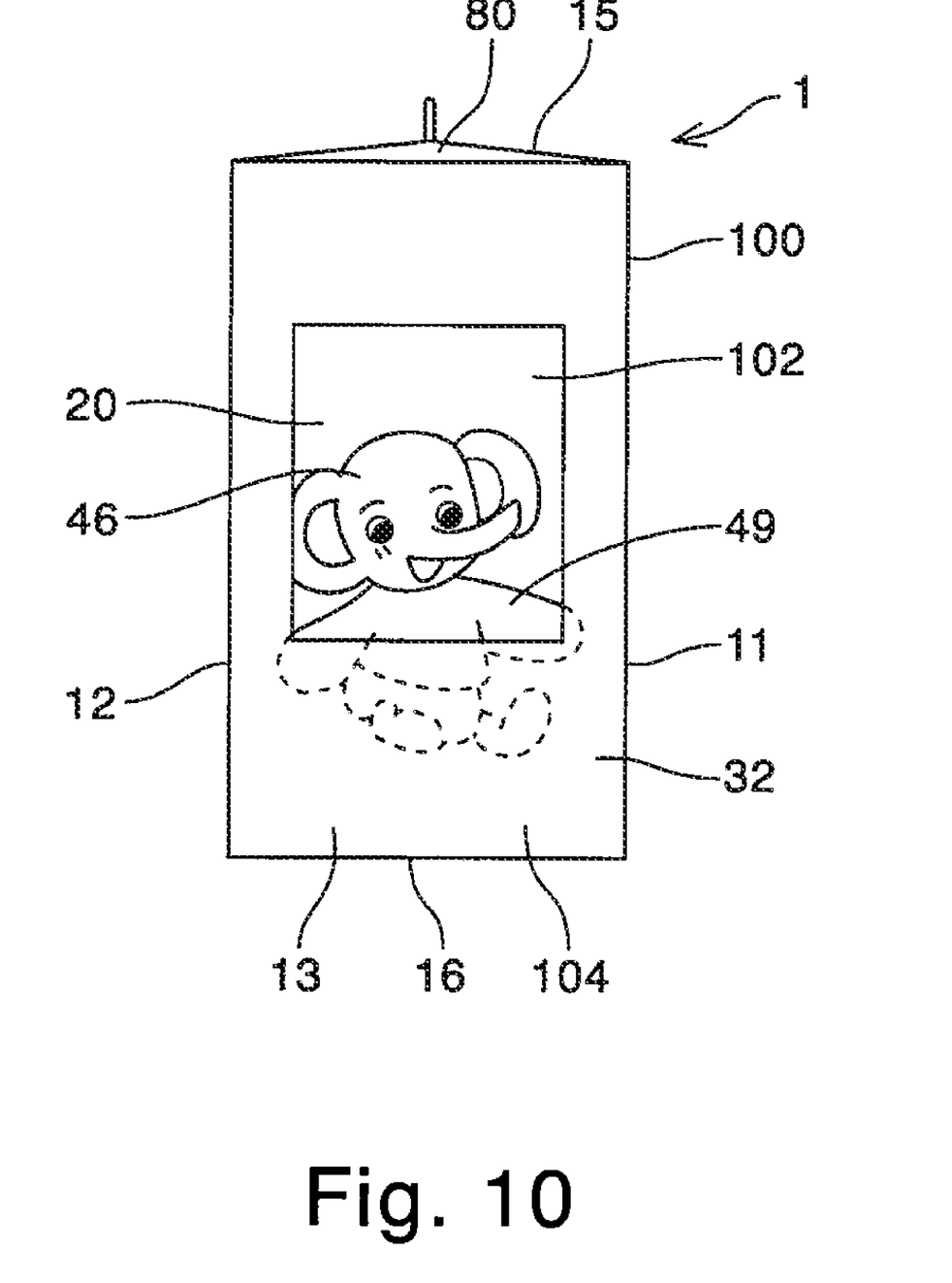
FIG. 10 illustrates an embodiment of a side view of the absorbent product seen from the first panel.

The term "primary element" may mean an integral part of the graphic that characterizes the contents of the graphic. When the integral part of the graphic is visible through the window area but the whole graphic is not visible through the window area, the integral part may help the viewer imagine and grasp the whole contents of the graphic to the viewer. By taking an example of the graphic comprising a cartoon character, a doll, a robot, an animal, a human being or the like, even if the peripheral part such as foot and hand are covered by the ultraviolet barrier area, a person may be able to imagine and grasp the whole contents of the graphic. In the embodiment of FIG. 10, the absorbent article 20 contained in the package 100 comprises a graphic 40 comprising a baby elephant 49. A face part 46 of the baby elephant 49 is perceivable through the first window area 102. The face part 46 may be a primary element because the contents of the graphic 40 can be identified as far as the face part 46 helps the viewer imagine and grasp that the graphic 40 comprises a baby elephant 49 although the other part of the graphic (e.g., hand, foot and the like) may not be visible through the first window area 102.

The term "design element" may mean a distinctive element of the graphic. For example, when the graphic 40 comprises a continuous pattern, a viewer may be able to grasp and imagine the other part of the continuous pattern if a part of the continuous pattern is perceivable through the window area. The continuous pattern may include, for example, polka dots, stripes, fabric design, landscapes, and the like. In the embodiment of FIG. 5, even if the whole graphic 40 is not visible through the first window area 102, a person may be able to imagine and grasp that the diaper 20 comprises the graphic 40 of polka dots by seeing the part of the graphic 40 through the first window area 102. In the embodiment of FIG. 6, the second window area 103 is so small that a person may find it difficult to imagine and grasp the whole graphic 40 in the rear region 54. In the embodiment of FIG. 7, the second panel 34 comprises no window area and the graphic 40 in the rear region 54 is not visible from outside of the package 100. In the embodiment of FIG. 8, as the second window area 103 is narrow, a person may find it difficult to imagine and grasp the whole graphic 40 by seeing a part of the graphic 40 through the second window area 103.

The graphic 40 in the front region 52 is more visible than the graphic 40 in the rear region 54 when a package 100 containing a plurality of absorbent articles 20 is viewed from outside. "More visible" may mean that the graphic feature (e.g., primary element and/or the design element) of one graphic is more perceivable by a viewer than another. Referring to FIG. 5, the absorbent product 1 comprises a diaper 20A whose front region 52 contacts the first panel 32 and a diaper 20B whose rear region 54 contacts the second panel 34. In order that the graphic 40 in the front region 52 of the diaper 20A may be more visible than the graphic 40 in the rear region 54 of the diaper 20B, the primary element of the graphic 40 and/or the design element of the graphic 40 in the front region 52 may be more perceivable than those of the graphic 40 in the rear region 54. In the embodiment of FIGS. 5 and 6, the first window area 102 as illustrated in FIG. 5 is larger than the second window 103 as illustrated in FIG. 6. The primary element and/or the design element of the graphic 40 in the front region 52 (refer to FIG. 5) may be more perceivable than those of the graphic in the rear region 54 (refer to FIG. 6). As a result, the graphic 40 in the front region 52 is more visible than the graphic 40 in the rear region 54. Also, in the embodiment of FIGS. 5 and 7, the first panel 32 as illustrated in FIG. 5 comprises a first window area 102 while the second panel 34 as illustrated in FIG. 7 comprises no window area. The primary element and/or the design element in the front region 52 are perceivable (refer to FIG. 5) while the primary element and/or the design element in the rear region 54 are not perceivable (refer to FIG. 7). Therefore, the graphic 40 in the front region 52 is more visible than the graphic 40 in the rear region 54. Furthermore, in the embodiment of FIGS. 5 and 8, the second panel 34 as illustrated in FIG. 8 comprises a second window 103 having an elongated shape and it may be difficult for a viewer to perceive the primary element or the design element of the graphic 40. In contrast, the first window 102 as illustrated in FIG. 5 is so large that the primary element and/or the design element of the graphic 40 in the front region 52 through the first window area 102 (refer to FIG. 5) may be more perceivable than those of the graphic 40 in the rear region 54 through the second window area 103 (refer to FIG. 8). Therefore, the graphic 40 of the front region 52 is more visible than the graphic 40 of the rear region 54.

The disposable tape 67 is disposed on the rear region 54 of the diaper 20. In the embodiment of FIG. 5, a plurality of diapers 20 are contained in the package 100 so that all the disposable tapes 67 therein may be directed to the same orientation to face the second panel 34. As the front region 52 of the diaper 20A faces the first panel 32, the rear region 54 of the diaper 20B faces the second panel 34. The disposable tape 67 of the diaper 20B as illustrated in FIG. 5 faces the second panel 14 (refer to FIGS. 6, 7 and 8). The disposable tape 67 facing the second panel 34 may be further covered by the ultraviolet barrier area 104. The disposable tape 67 may at least partially face the second window area 103.

Figure 11:
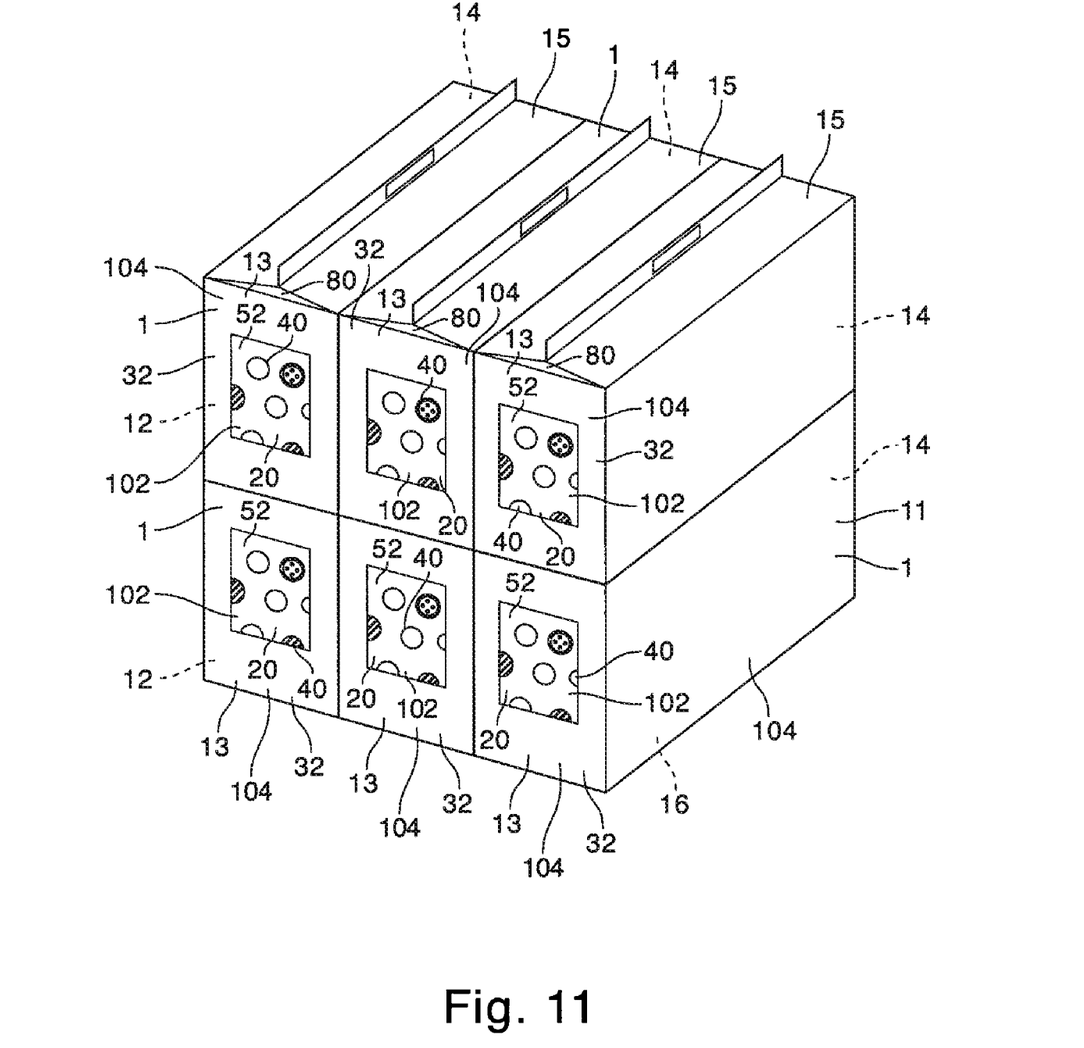
FIG. 11 illustrates an embodiment of a display for the absorbent products comprising a plurality of absorbent articles inside.

FIG. 11 illustrates an embodiment of a display of the absorbent product 1 outside the store. The second panel 34 of the absorbent product 1 as illustrated in FIG. 11 is the same as illustrated in FIG. 8 (the second window area 103 has an elongated shape). The graphic 40 of the front region 52 is more visible than the graphic 40 of the rear region 54. The visibility of the graphic 40 of the front region 52 may make the consumers feel inclined to purchase the absorbent product 1. Therefore, the retailers may be motivated to display the absorbent product 1 so that the side of the first panel 32 (i.e., the graphic 40 of the front region 52) faces toward the consumers. The first panel 32 facing toward the consumers may receive the ultraviolet ray depending on the atmosphere of display. As the disposable tape 67 faces the second panel 34 opposite to the first panel 32, the disposable tape 67 may receive less ultraviolet ray and the disposable tape 67 may be less affected by the ultraviolet ray. As the disposable tape 67 is protected from the ultraviolet ray, the appearance and quality of the absorbent article is maintained (e.g. protection from discoloration, stiffening, loss of adhesibility and the like) even after a long-time exposure to the ultraviolet ray, for example by displaying outside the store where a sun-shade is not available.

Test Methods

This section describes the methods for determining the light transmittance and the ultraviolet transmittance of a sheet material.

1. Light Transmittance

In the measurement, UV-VIS-NIR spectrophotometer (Shimadzu Corporation, UV-3600) is used to retrieve the desired light source of the experiment. This UV-VIS-NIR spectrophotometer includes a light source which has a halogen lamp, a sample holder, spectrometers, detector units which consist of a photomultiplier, InGaAs photo diode and PbS cell, and a computer. The light source is placed away from one side of the sample holder, while the detector is placed away from the other side of the sample holder in the path of the light.

In the measurement, the halogen lamp turns on. A sample sheet material is held by the sample holder so that it receives the light irradiated from the halogen lamp in the effective measurement area. The light passes through the sample sheet material and reaches the detector. The sample light volume (Vs) and the reference light volume (Vr) without a sample are then measured by the detector and recorded by the computer. This process is repeated for one sample sheet material at least three times and the average values of the light volumes (Vrav and Vsav) are calculated and recorded by the computer. The computer then calculates the light transmittance (LT) by the following formula:

$$LT(\%) = (Vsav/Vrav) \times 100 \quad (I)$$

2. Ultraviolet Transmittance Test

The measurement is carried out by the same procedure as the light transmittance test using UV-VIS-NIR spectrophotometer (Shimadzu Corporation, UV-3600) except that the ultraviolet ray in the wavelength range between 250 mm and 400 mm is retrieved. The ultraviolet transmittance is measured at the wavelength of 340 nm.

It is understood that the examples and embodiments described herein are for illustrative purpose only and that various modifications or changes will be suggested to one skilled in the art without departing from the scope of the present invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent product comprising:
    (i) a package comprising a first panel and a second panel opposed to the first panel, the package comprising a first window area in the first panel, a second window area in the second panel, and an ultraviolet barrier area at least partially disposed in the second panel, the ultraviolet barrier area comprising an ultraviolet absorbing agent; and
    (ii) a plurality of absorbent articles which are stacked and contained in the package;
        each of the absorbent articles having a body facing surface and an external surface opposed to the body facing surface; each of the absorbent articles having a front region and a rear region opposed to the front region; each of the absorbent articles comprising a liquid permeable topsheet, a liquid impermeable backsheet, an absorbent core disposed between the topsheet and the backsheet, and a disposable tape secured to the external surface of the rear region; each of the absorbent articles comprising a graphic in the front region and in the rear region; the front region facing the first panel and the rear region facing the second panel; the graphic of the front region being visible through the first window area and the disposable tape being covered by the ultraviolet barrier area; wherein the graphic of the front region is more visible than the graphic of the rear region when viewed from outside.

2. The absorbent product of claim 1 wherein a graphic feature of the front region is more perceivable than a graphic feature of the rear region.

3. The absorbent product of claim 2 wherein the graphic feature is a primary element of the graphic or a design element of the graphic.

4. The absorbent product of claim 1 wherein the first window area is larger than the second window area.

5. The absorbent product of claim 1 wherein the first window area allows more light transmittance than the second window area.

* * * * *